United States Patent [19]

Tsuda et al.

[11] Patent Number: 5,059,628

[45] Date of Patent: Oct. 22, 1991

[54] MEDICAL COMPOSITION FOR PERCUTANEOUS ADMINISTRATION

[75] Inventors: Yoko Tsuda; Susumu Satoh; Tetsuo Omata, all of Osaka, Japan

[73] Assignee: Nitto Electric Industrial Co., Ltd., Osaka, Japan

[21] Appl. No.: 494,843

[22] Filed: Mar. 14, 1990

Related U.S. Application Data

[63] Continuation of Ser. No. 101,604, Sep. 28, 1987, abandoned.

[51] Int. Cl.$^5$ .............................................. A01N 25/00
[52] U.S. Cl. .................................... 514/784; 514/785; 514/947
[58] Field of Search ............... 514/423, 428, 946, 947, 514/422, 784, 785

[56] References Cited

U.S. PATENT DOCUMENTS 4,789,667 12/1988 Makino et al. ...................... 514/161
4,863,952 9/1989 Abe et al. ............................ 514/423

FOREIGN PATENT DOCUMENTS 0182635 5/1986 European Pat. Off. .
3536669 4/1986 Fed. Rep. of Germany .

OTHER PUBLICATIONS

Chemical Abstracts, vol. 103, Nos. 2 & 3, 7/22/85, p. 50, Abstract No. 16739d.

*Primary Examiner*—Frederick E. Waddell
*Assistant Examiner*—T. J. Criares
*Attorney, Agent, or Firm*—Sughrue, Mion, Zinn, Macpeak & Seas

[57] ABSTRACT

A medical composition for external use comprising a proline ester represented by formula (I):

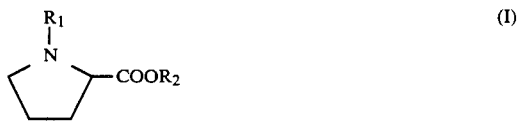

wherein $R_1$ and $R_2$ are as defined in the specification, or a prolinol ester represented by formula (II):

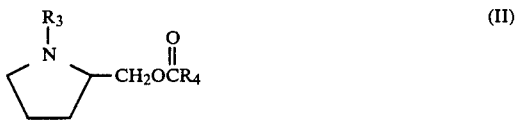

wherein $R_3$ and $R_4$ are as defined in the specification. The composition enhances percutaneous penetration absorption of an active ingredient to be combined therewith.

4 Claims, No Drawings

MEDICAL COMPOSITION FOR PERCUTANEOUS ADMINISTRATION

This is a continuation of application Ser. No. 101,604, filed Sept. 28, 1987, now abandoned.

FIELD OF THE INVENTION

This invention relates to medical compositions for percutaneous administration of phsiologically ingredients (hereafter often merely an "active ingredient(s)" for brevity) and a method for accelerating percutaneous absorption of active ingredients using the same.

BACKGROUND OF THE INVENTION

External application of active ingredients has been intended to produce local effects, such as bactericidal effects, disinfectious effects, analgesic effects, antipsoraic effects, antiinflammatory effects, and the like, onto the skin or subcutaneous tissues.

On the other hand, oral administration or injection commonly aims at producing systemic effects. Oral administration sometimes associates with problems that the absorbed active ingredient is susceptible to primary metabolism in the liver and that the oral administration of active ingredient in order to assure long-lasting effects gives- temporary higher than desired blood level, resulting in unfavorable side effects. Further, some active ingredients, for example, Indometacine, cause gastrointestical disorders when administered orally.

Administration by injections achieves rapid absorption of active ingredients but requires specialists, such as physicians.

In order to overcome the above-described disadvantages of oral administration or injection, percutaneous administration aiming at systemic effects has recently been proposed. Percutaneous administration of active ingredients is advantageous in that desired blood level of active ingredients can be maintained easily so that duration of therapy can be easily controlled and that primary metabolism of active ingredient by the liver can be eliminated.

However, since normal skin naturally has a barrier function to prevent entrance of a foreign matter into the body, normal skin is relatively impermeable to most therapeutic agents in that desired blood levels of the therapeutic agent cannot be achieved by means of percutaneous absorption. The percutaneous absorption of therapeutic agents can, however, be enhanced by means of adjuvants or penetration enhancers, and various kinds of penetration enhancer have been proposed in recent years. For example, U.S. Pat. No. 3,551,554 discloses dimethyl sulfoxide as well as dimethylacetamide, dimethylformamide, methyldecyl sulfoxide, etc.

There are also known penetration enhancer compositions, such as a combination of dimethylacetamide with ethyl alcohol, isopropyl alcohol or isopropyl palmitate as disclosed in U.S. Pat. No. 3,472,431; a combination of 2-pyrrolidone with an suitable oil and an alcohol ester of a straight chain fatty acid as disclosed in U.S. Pat. No. 4,017,641; and the like. However, none of these penetration enhancer is satisfactory in effect, safety, and feel on use.

SUMMARY OF THE INVENTION

One object of this invention is to provide a medical composition for percutaneous administration which enhances percutaneous penetration and absorption of active ingredients.

Another object of this invention is to provide a method for enhancing percutaneous penetration and absorption of active ingredients.

As a result of extensive investigations, it has now been found that the above objects of the present invention can be accomplished by a proline ester represented by formula (I) hereinafter described or a prolinol ester represented by formula (II) hereinafter described. The proline ester or prolinol ester according to the present invention enhances percutaneous penetration and absorption of active ingredients, and their effects are synergistically increased when combined with a polar compound.

The present invention provides a medical composition for percutaneous administration which contains a proline ester represented by formula (I):

wherein $R_1$ represents a hydrogen atom or an aliphatic hydrocarbon residue, and $R_2$ represents an aliphatic hydrocarbon residue, with the proviso that the total number of carbon atoms in $R_1$ and $R_2$ is 20 or less and a nitrogen atom in 5-membered ring may be quaternarized to form salt thereof, or a prolinol ester represented by formula (II):

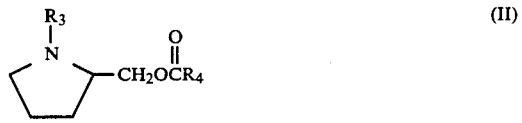

wherein $R_3$ represents a hydrogen atom or an aliphatic hydrocarbon residue, and $R_4$ represents an aliphatic hydrocarbon residue, with the proviso that the total number of carbon atoms in $R_3$ and $R_4$ is 18 or less, and a nitrogen atom in 5-membered ring may be quaternarized to form salf thereof.

The present invention further provides a method for enhancing percutaneous penetration and absorption of an active ingredient, which comprises percutaneously administering the active ingredient in the presence of a proline ester represented by formula (I) or a prolinol ester represented by formula (II).

DETAILED DESCRIPTION OF THE INVENTION

The term "aliphatic hydrocarbon residue" as used herein means a saturated or unsaturated and straight, branched chain or cyclic hydrocarbon group.

The term "lower alkyl group" as used herein means a straight or branched chain group and includes alkyl groups having from 1 to 5 carbon atoms, e.g., a methyl group, an ethyl group, an n-propyl group, an isopropyl group, an nbutyl group, etc.

In formula (I), the aliphatic hydrocarbon residue as represented by $R_1$ or $R_2$ preferably contains from 1 to about 20 carbon atoms, and more preferably from 1 to 18 carbon atoms. The total number of carbon atoms contained in $R_1$ and $R_2$ should not exceed 20.

The unsaturated hydrocarbon group preferably contains 1 or 2 unsaturated bonds, and the unsaturated bond is preferably a double bond. The cyclic hydrocarbon group as represented by $R_1$ or $R_2$ preferably includes a 5- to 7-membered monocyclic group which preferably contain from 5 to 12 carbon atoms.

In formula (II), the aliphatic hydrocarbon group as represented by $R_3$ or $R_4$ preferably contains from 1 to about 18 carbon atoms. The total number of carbon atoms contained in $R_3$ and $R_4$ should not exceed 18.

The unsaturated hydrocarbon group preferably contains 1 or 2 unsaturated bonds, and the unsaturated bond is preferably a double bond. The cyclic hydrocarbon group preferably contains a 5- to 7-membered monocyclic ring which preferably contains from 6 to 12 carbon atoms.

More specifically, the aliphatic hydrocarbon residue as represented by $R_1$ in formula (I) or $R_3$ in formula (II) includes lower alkyl groups having from 1 to 5 carbon atoms, e.g., a methyl group, an ethyl group, an n-propyl group, an isopropyl group, an n-butyl group, a sec-butyl group, a t-butyl group, an n-amyl group, an isoamyl group, etc.

The aliphatic hydrocarbon residue as represented by $R_2$ or $R_4$ includes saturated acyclic groups having from 6 to 18 carbon atoms, e.g., an n-hexyl group, an n-heptyl group, an n-octyl group, an n-nonyl group, an n-decyl group, an n-undecyl group, an n-dodecyl group, an n-tridecyl group, an n-tetradecyl group, an n-hexadecyl group, an n-octadecyl group, a 2-methylhexyl group, a 2-ethylhexyl group, a 3,7-dimethyloctyl group, a 2-hexyldecyl group, a 2,4,4-trimethylpentyl group, etc.; saturated cyclic groups, e.g., a 2-cyclohexylethyl group, a cycloheptyl group, a cyclohexylmethyl group, a 4-cyclohexylbutyl group, a 3-cyclopentylpropyl group, etc.; and unsaturated acyclic groups, e.g., a cis-3-hexenyl group, a 2-decenyl group, an oleyl group, a menthyl group, a geranyl group, etc.

The proline esters of formula (I) and prolinol esters of formula (II) may be in the form of a pharmaceutically acceptable salt formed by quaternarizing the nitrogen atom in the 5-membered ring. The pharmaceutically acceptable salt includes those formed with organic acids, e.g., citric acid, tartaric acid, succinic acid, maleic acid, fumaric acid, etc., and those formed with inorganic acids, e.g., hydrochloric acid, hydrobromic acid, sulfuric acid, nitric acid, phosphoric acid, etc.

The compounds according to the present invention are substantially known per se and can be prepared by known processes or processes analogous thereto.

For example, the prolinol ester of formula (II) can be synthesized by reaction of a reactive derivative of an aliphatic carboxylic acid represented by formula (III):

wherein $R_4$ is as defined above [e.g., an acid halide (e.g., acid chloride), an acid anhydride, a mixed acid anhydride, an active ester, etc.] and a compound represented by formula (IV):

wherein $R_3$ is as defined above.

The reaction can be carried out under known conditions. When the prolinol esters wherein $R_3$ is a hydrogen atom are synthesized by esterificatin of the compounds of formula (IV) wherein $R_3$ is a hydrogen atom, i.e., prolinol, it is preferable that the amino group of the starting prolinol is protected with an appropriate protective group prior to the esterification and the protective group is released after completion of the esterification. The protective group which can be used is not particularly limited as long as it is not removed during the esterification but removable after the esterification. Examples of such a protective group include a carbobenzoxy group, a t-butoxycarbonyl group, etc.

The starting compound of formula (IV) wherein $R_3$ is an aliphatic hydrocarbon residue can be obtained, for example, from the compound of formula (IV) wherein $R_3$ is a hydrogen atom (i.e., prolinol) in accordance with the process described in Chavdarian, Charles G. and Sanders, Edward B., *Org. Prep. Proced. Int.*, Vol. 13, No. 6, 389–393 (1981) or analogous processes.

The proline esters of formula (I) can also be synthesized by known processes, e.g., the processes described in Bull. Soc. Chim., Nos. 7–8, 2460–2466 (1973), Beilstein, *Handbuch der Organishen Chemie*, 1st Ed., Vol. 14, p. 165 and Vol. 20, pp. 25, 60, and 62, ibid, 3rd Ed., Vol. 20, p.38, and processes analogous thereto.

It is preferable that the composition according to the present invention further contains polar compound(s). It was confirmed that the percutaneous penetration of active ingredients with the compounds of the present invention can be synergistically enhanced when combined with the polar compound.

The polar compounds which can be used in the present invention preferably include (1) lower alcohols, (2) glycerin or esters thereof, (3) thioglycerols, (4) lactic esters, (5) ethyleneurea derivatives represented by formula (V):

wherein $R_5$ and $R_6$ each represents a hydrogen atom or a lower alkyl group, (6) amid compounds represented by formula (VI):

wherein $R_7$, $R_8$, and $R_9$ each represents a hydrogen atom or a lower alkyl group, (7) alkylene glycols, (8) mono- or diethyelne glycol monoalkyl ethers, (9) lactones, (10) pyrrolidone compounds represented by formula (VII):

wherein $R_{10}$ represents a hydrogen atom or a lower alkyl group, and (11) lactam compounds represented by formula (VIII):

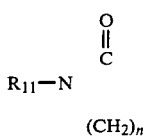

(VIII)

wherein $R_{11}$ represents a lower alkyl group; and n represents 4 or 5.

In formulae (V) to (VIII), the lower alkyl group as represented by $R_5$, $R_6$, $R_7$, $R_8$, $R_9$, $R_{10}$, and $R_{11}$ preferably includes those having from 1 to 4 carbon atoms, e.g., a methyl group, an ethyl group, a propyl group, an isopropyl group, an n-butyl group, etc.

Specific examples of the lower alcohols which can be used preferably are those .having from 1 to 6 carbon atoms, such as methyl alcohol, ethyl alcohol, n-propyl alcohol, isopropyl alcohol, n-butyl alcohol, isobutyl alcohol, sec-butyl alohol, t-butyl alcohol, n-amyl alcohol, isoamyl alcohol, n-hexyl alcohol, cis-3-hexenol, etc.

The glycerin esters may be any of mono-, di- and triesters. The acid moiety of the glycerin esters preferably includes fatty acids having from 2 to 6 carbon atoms, and more preferably acetic acid. Specific examples of the glycerin esters are glycerin monoacetate, glycerin diacetate, etc.

The thioglycerols may be any of mono- di- and triglycerols. Specific examples include α-monothioglycerol.

The lactic esters preferably include those having from 1 to 4 carbon atoms in their alkyl moiety, e.g., methyl lactate, ethyl lactate, propyl lactate, butyl lactate, etc.

Specific examples of the ethyleneurea derivatives of formula (V) are N,N'-dimethylethyleneurea, N,N'-diethylethyleneurea, etc.

Specific examples of the amid compounds of formula (VI) are formamide, N-methylformamide, N,N-dimethylformamide, N,N-diethylformamide, acetamide, N-methylacetamide, N,N-dimethylacetamide, N,N-diethylacetamide, propionamide, N-methylpropionamide, N,N-dimethylpropionamide, N,N-diethylpropionamide, etc.

The alkylene glycols preferably include those having from 2 to 8 carbon atoms in their alkylene moiety. Specific examples of the alkylene glycols are ethylene glycol, 1,3-propanediol, 1,2-propanediol, butanediol, pentanediol, 2-methyl-2,4-pentanediol, 2-ethyl-1,3-hexanediol, etc.

The mono- or diethylene glycol monoalkyl ethers preferably include those containing from 1 to 2 carbon atoms in their alkyl moiety, e.g., ethylene glycol monomethyl ether, ethylene glycol monoethyl ether, etc.

The lactones preferably include 4- and 5-membered rings, e.g., propiolactone, butyrolactone, etc.

Specific examples of the pyrrolidone compounds of formula (VII) are 2-pyrrolidone, N-methylpyrrolidone, etc.

Specific examples of the lactam compounds of formula (VIII) are N-methylpiperidone, N-methylcaprolactam, etc.

These polar compounds are preferably used in an amount of from 30 to 99.5%, and more preferably from 50 to 99%, by weight based on the total amount of the proline ester or prolinol ester and the polar compound(s).

Since the composition according to the present invention is effective to accelerate percutaneous absorption of an active ingredient, effective percutaneous absorption of an active ingredient into the body can be achieved by external application of the active ingredient to the skin in the presence of the composition of the present invention. In a preferred mode of application, the active ingredient to be administered is previously compounded with the composition.

Any of active ingredients that are externally applicable, whether for topical effects or for systemic effects, can be combined with the composition of the present invention. The active ingredients to be administered preferably have a molecular weight of less than 1000, and more preferably less than 500. According to the present invention, those active ingredients having their chief aim at production of topical effects can penetrate deep into the skin, and those active ingredients having their chief aim at production of systemic effects can be rapidly transferred to the blood.

The active ingredients for topical effects include topical anesthetics, e.g., procain hydrochloride, tetracain hydrochloride, dibucain hydrochloride, lidocain, lidocain hydrochloride, piperocain acetate, etc.; antihistaminics, e.g., diphenhydramine hydrochloride, chlorpheniramine maleate, brompheniramine maleate, diphenylimidazole, clemizole hydrochloride, etc.; antibiotics, e.g., lincomycin, penicillin G, erythromycin, tetracyclin hydrochloride, clindamycin, kanamycin, oxytetracycline, chloramphenicol, fragiomycin, nystatin, gramicidin hydrochloride, bacitracin, etc.; antifungals, e.g., gliserofulvin, N-methyl-N-(3-tolyl)thiocarbamic acid 2-naphthyl ester, diametazole hydrochloride, aureothricin, trichomycin, pyrrolnitrin, 5-fluorocytosine, etc.; and the like.

The active ingredients for systemic effects include benzodiazepines, e.g., diazepam, nitrazepam, lorazepam, prazepam, fludiazapam, clonazepam, etc.; diuretics, such as thiazides, e.g., bendroflumethiazioe, polythiazide, methyclothiazide, trichlormethiazide, cyclopenthiazide, bentylhydrochlorothiazide, hydrochlorothiazide, bumetanide, etc.; antihypertensives, e.g., clonidine, ACE inhibitors(eg. captopril, enalapril, etc), etc.; antihistaminics, such as amino ethers, diphenhydramine, carbinoxamine, diphenylpyraline, etc., ethylenediamines, e.g., phenbenzamine, etc., monoamines, e.g., chlorpheniramine, etc.; non-steroidal antiinflammatory agents, e.g., indometacine, ibuprofen, ibufenac, alclofenac, diclofenac, mefenamic acid, flurbiprofen, flufenamic acid, ketoprofen, sodium salicylate, etc.; anti-tumor agents, e.g., 5-fluorouracil, 1-(2-tetrahydrofuryl)-5-fluorouracil, cytarabine, broxuridine, etc.; corticosteroid anti-inflammatory agents, e.g., cortisone, hydrocortisone, prednisolone, prednisone, triamcinolone, dexamethasone, betamethasone, etc.; antiepileptics, e.g., ethosuximide, etc.; antiarrhythmics, e.g., ajmalin, prajmalin, pindolol, propranolol, quinidine, etc.; psyconeurotropics, e.g., clofluperirol, trifluperidol, haloperidol, moperone, scopolamines (e.g., methylscopolamine, butylscopolamine, etc.), metoclopramide hydrochloride,, clorpromazine, atropines (e.g., atropine methylbromide, anisotropine methylbromide, etc.), etc.; vasodilators, e.g., isosorbide dinitrate, nitroglycerin, pentaerythritol tetranitrate, propatylnitrate, dipyridamole,Ca channel blockers (eg. nifedipine, diltiazem, verapamil, etc.) etc.; and antibiotics, such as tetracyclines (e.g., tetracycline, oxytetracycline, metacycline, doxycycline, minocycline, etc.), chloramphenicols, erythromicines, etc.

The amount of the active ingredient to be incorporated is such an amount enough to exhibit desired pharmacological effects and can be selected appropriately depending on the kind of the active ingredient, the body weight of the patient, symptoms, and the like. In general, the active ingredient is incorporated in an amount of from 0.01 to 20%, and preferably 0.2 to 10%, by weight based on the total weight of the proline ester or prolinol ester with/without the polar compound. The above-recited range is not so critical because the amount of the active ingredient to be administered can be controlled by increasing or decreasing the area to which the active ingredient-containing composition is applied.

The external composition according to the present invention may be applied to the skin as it is or in various formulations. Dosage forms for external use include ointments, plasters, lotions, adhesive tapes, impregnants, gels, etc. Of these, the impregnants can be prepared by, for example, impregnating the composition of the present invention which may contain known additives into an appropriate absorbent such as gauze, filter paper, porous membrane, and the like. Such impregnants are usually applied to the skin with an aid of an adhesive tape. The gels can be prepared by, for example, geling the composition of the invention by using, e.g., dibenzylidene sorbitol (e.g., "Gelol D" produced by New Japan Chemical Co., Ltd.) and spreading the gel onto backing materials, eg, a plastic film. The adhesive base for adhesive tape or plaster formulations which may contain the active ingredient and the composition includes acrylic copolymers, polyvinyl ether compounds, rubbery adhesive mixtures, etc. Other forms of external preparations can be prepared easily by known means.

The proline esters or prolinol esters according to the present invention have an effect to enhance preparation and absorption of the active ingredient through the skin. Therefore, percutaneous penetration and absorption of active ingredients can be enhanced by administration in the presence of the compounds of the present invention. Further, the combination of the proline ester or prolinol ester and polar compound(s) brings synergistic effects on percutaneous penetration and absorption of the active ingredient. Therefore, the composition further containing the polar compound(s) achieves higher efficiency of percutaneous absorption of active ingredients.

The present invention is illustrated in greater detail with reference to the following Reference Examples, Examples, and Test Examples, but it should be understood that the present invention is not deemed to be limited thereto.

REFERENCE EXAMPLE 1

To 64.5 g of n-dodecyl alcohol was added dropwise 6.8 ml of thionyl chloride under ice-cooling. After the addition, the temperature of the reaction mixture was raised to room temperature, and crystals of l-proline were added to the reaction mixture. The mixture was heated at 70° C. to effect reaction for 5 hours. After completion of the reaction, the excess of n-dodecyl alcohol was separated by column chromatography, and the resulting proline n-dodecyl ester weighing 10.4 g was purified by distillation (b.p.=114.5° C./0.05 mmHg).

REFERENCE EXAMPLES 2 TO 8

Proline esters having various groups as $R_2$ in formula (I) as shown in Table 1 below were synthesized in the same manner as in Reference Example 1, except for changing n-dodecyl alcohol to the corresponding alcohol.

TABLE 1

| Reference Example No. | $R_2$ | Product |
|---|---|---|
| 2 | $-(CH_2)_5CH_3$ | proline n-hexyl ester |
| 3 | $-(CH_2)_7CH_3$ | proline n-octyl ester |
| 4 | $-(CH_2)_9CH_3$ | proline n-decyl ester |
| 5 | $-(CH_2)_{13}CH_3$ | proline n-tetradecyl ester |
| 6 | $-(CH_2)_{17}CH_3$ | proline n-octadecyl ester |
| 7 | $-CH_2CH(CH_2)_3CH_3$<br>$\quad\mid$<br>$\quad C_2H_5$ | proline 2-ethylhexyl ester |
| 8 | $-CH_2CH=CH(CH_2)_6CH_3$ | proline 2-decenyl ester |

REFERENCE EXAMPLE 9

Lauryl hygrate (N-methylproline lauryl ester) was synthesized in the same manner as in Reference Example 1, except for replacing proline with hygric acid.

REFERENCE EXAMPLE 10

In 150 ml of ethanol was dissolved 22.8 g of ethyl 2,5-dibromovalerate, and 15 g of potassium carbonate was suspended in the solution. To the suspension was added dropwise a methanolic solution of 18.5 g of laurylamine under ice-cooling. After the addition, the reaction mixture was allowed by react at a refluxing temperature of methanol for 5 hours to obtain N-dodecylproline ethyl ester.

REFERENCE EXAMPLES 11 TO 16

Proline esters having various groups as $R_1$ in formula (I) as shown in Table 2 below were synthesized in the same manner as in Reference Example 10.

TABLE 2

| Reference Example No. | $R_1$ | Product |
|---|---|---|
| 11 | $-(CH_2)_5CH_3$ | N-hexylproline methyl ester |
| 12 | $-(CH_2)_{13}CH_3$ | N-tetradecylproline ethyl ester |
| 13 | $-(CH_2)_{11}CH_3$ | N-dodecylproline octyl ester |
| 14 | $-(CH_2)_5CH_3$ | N-hexylproline hexyl ester |
| 15 | 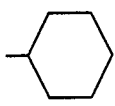 | N-cyclohexylproline decyl ester |
| 16 | $-CH_2CH(CH_2)_3CH_3$<br>$\quad\mid$<br>$\quad C_2H_5$ | N-2-ethylhexylproline methyl ester |

The $R_2$ moiety of the above proline esters can easily be introduced by interesterification between the corresponding proline esters synthesized according to the process of Reference Example 10 with the corresponding alcohol.

EXAMPLES 12 TO 33

| Basic Formulation: | |
|---|---|
| (1) Active ingredient | 1 wt % |
| (2) Polar compound | 89 wt % |
| (3) Proline ester of formula (I) | 10 wt % |

A medical composition for external use was prepared by mixing the components (2) and (3) and then dissolving the component (1) in the liquid mixture.

| Control Formulation; | |
|---|---|
| (1) Active ingredient | 1 wt % |
| (2) Dimethyl sulfoxide | 99 wt % |

A medical composition for external use was prepared by dissolving the component (1) in the component (2).

The kinds of the above components in basic and control formulations are shown in Table 5.

COMPARATIVE EXAMPLES 1 to 7

| (1) Active ingredient | 1 wt % |
|---|---|
| (2) Polar compound | 99 wt % |

The component (1) was dissolved in the component (2) to prepare a medical composition for external use. The kinds of the components (1) and (2) are shown in Table 6.

EXAMPLES 34 TO 37

| (1) Propranolol hydrochloride | 1 wt % |
|---|---|
| (2) N-Methylpyrrolidone | 94 to 98.5 wt % |
| (3) Proline n-dodecyl ester | 0.5 to 5 wt % |

The components (2) and (3) were mixed in amounts shown in Table 7, and the component (1) was dissolved therein to prepare a medical composition for external use.

EXAMPLES 38 TO 40

| (1) Propranolol hydrochloride | 1 wt % |
|---|---|
| (2) N-Methylpyrrolidone | 94 to 98.5 wt % |
| (3) N-Methylproline n-dodecyl ester | 0.5 to 5 wt % |

The components (2) and (3) were mixed in amounts shown in Table 8, and the component (1) was dissolved therein to prepare a medical composition for external use.

EXAMPLES 41 TO 46

| (1) Active ingredient | 1 wt % |
|---|---|
| (2) Polar compound | 89 wt % |
| (3) Proline n-dodecyl ester hydrochloride | 10 wt % |

A medical composition for external use was prepared by mixing the components (2) and (3) and dissolving the component (1) in the mixture. The kinds of the components (1) and (2) are shown in Table 9.

REFERENCE EXAMPLE 17

To a benzene solution containing 5.0 g (0.023 mol) of tridecanoic acid was added 25 g of thionyl chloride, followed by refluxing for 5 hours. The excess of thionyl chloride and benzene were removed by distillation to obtain tridecanoyl chloride.

To a benzene solution containing 5.4 g of N-carbobenzoxyprolinol was added 1.8 g of pyridine, and the above-prepard tridecanoyl chloride was added dropwise thereto under ice-cooling. After stirring at room temperature for 2 hours, the reaction mixture was poured into a saturated aqueous solution of sodium bicarbonate. The reaction mixture was extracted with benzene, and the benzene layer was washed successively with water and a saturated sodium chloride aqueous solution, and dried over sodium sulfate. The benzene was removed by distillation, and the residue was purified by column chromatography to obtain 7.1 g of tridecanoic acid N-carbobenzoxy-2-pyrrolidine methyl ester.

The resulting product was dissolved in methanol and catalytically hydrogenated using palladium-on-carbon as a catalyst at room temperature for 3 hours. The reaction mixture was filtered through Celite to remove the catalyst, and the filtrate was distilled to remove methanol. The residue was purified by column chromatography to obtain 3.4 g (yield: 49% from tridecanoic acid) of a prolinol ester of formula (II) wherein $R_3=H$ and $R_4=-(CH_2)_{11}CH_3$.

REFERENCE EXAMPLES 18 TO 21

Prolinol esters of formula (II) as shown in Table 3 below were synthesized in the same manner as in Reference Example 17. The yield based on the starting carboxylic acid is also shown in Table 3.

TABLE 3

| Reference Example No. | $R_3$ | $R_4$ | Yield (%) |
|---|---|---|---|
| 18 | H | $n-C_6H_{13}$ | 47 |
| 19 | H | $n-C_8H_{17}$ | 51 |
| 20 | H | $n-C_{15}H_{31}$ | 52 |
| 21 | H | $n-C_{17}H_{35}$ | 43 |

REFERENCE EXAMPLE 22

Five grams (0.050 mol) of prolinol were treated with double the equivalent of n-butyl lithium in tetrahydrofuran at $-70°$ C., and 7.0 g of methyl iodide was added dropwise thereto at $-70°$ C., followed by stirring for 2 hours. The temperature was gradually elevated, and the reaction was further continued for an additional hours under ice-cooling. To the reaction mixture was added 1.8 g of water, and the precipitate thus formed was removed by filtration. The filtrate was concentrated, and the concentrate was purified by column chromatography to obtain 3.0 g of N-methylprolinol.

The resulting N-methylprolinol (3.0 g; 0.026 mol) was mixed with 5.6 g (0.026 mol) of tridecanoic acid, and a catalytic amount of p-toluenesulfonic acid was added thereto. The reaction mixture was azeotripically dehydrated in benzene for 3 hours. A saturated aqueous solution of sodium bicarbonate was added to the reaction mixture, and the mixture was extracted with benzene. The benzene extract was washed successively with water and a saturated sodium chloride aqueous solution, and dried over sodium sulfate. The benzene was removed by distillation, and the residue was purified by column chromatography to obtain 6.1 g (yield: 39% from prolinol) of a prolinol ester of formula (II) wherein $R_3=CH_3$ and $R_4=-(CH_2)_{11}CH_3$.

REFERENCE EXAMPLES 23 TO 26

Prolinol esters of formula (II) having various groups as $R_3$ and $R_4$ as shown in Table 4 below were synthesized in the same manner as in Reference Example 22.

TABLE 4

| Reference Example No. | $R_3$ | $R_4$ | Yield (%) |
|---|---|---|---|
| 23 | $CH_3-$ | $CH_3(CH_2)_7CH=CH(CH_2)_7-$ | 42 |
| 24 | $CH_3-$ | cyclohexyl- | 31 |
| 25 | $C_2H_5-$ | $(CH_3CH_2CH_2)_2CH-$ | 36 |
| 26 | $n-C_5H_{11}-$ | $n-C_{12}H_{25}-$ | 26 |

EXAMPLES 47 TO 81

| Basic Formulation: | |
|---|---|
| (1) Active ingredient | 1 wt % |
| (2) Polar compound | 89 wt % |
| (3) Prolinol ester of formula (II) | 10 wt % |

A medical composition for external use was prepared by mixing the components (2) and (3) and dissolving the component (1) in the mixture. The kinds of the components (1) to (3) are shown in Table 10.

| Control Formulation: | |
|---|---|
| (1) Active ingredient | 1 wt % |
| (2) Dimethyl sulfoxide | 99 wt % |

A medical composition for external use was prepared by dissolving the component (1) in the component (2).

COMPARATIVE EXAMPLES 8 to 17

| (1) Active ingredient | 1 wt % |
|---|---|
| (2) Polar compound | 99 wt % |

A medical composition for external use was prepared by dissolving the component (1) in the component (2). The kinds of the components (1) and (2) are shown in Table 11.

TEST EXAMPLE

Each of the medical compositions prepared in Examples 1 to 81 inclusive of both basic formulations and control formulations and Comparative Examples 1 to 17 was evaluated for percutaneous permeability of the active ingredient as follows.

The skin cut from the abdomen of rats was fixed to a glass-made cell in such a manner that the surface side of the skin might contact with the composition while the back side contacting with a physiological saline. The amount of the active ingredient which had been permeated into the saline through the skin was qauantitatively determined by high performance liquid chromatography. The tests were carried out in a closed container. The permeability of the active ingredient through the skin was evaluated by obtaining a Q value from equation:

$$Q=C/D$$

wherein C is an amount of the active ingredient having been permeated through the skin in Examples or Comparative Examples; and D is that in Control Formulations. The results obtained are shown in Tables 5 to 11.

TABLE 5

| Example No. | (1) Active Ingredient | (2) Polar Compound | (3) Proline Ester (I) | Q value |
|---|---|---|---|---|
| 1 | propranolol hydrochloride | ethanol | proline n-hexyl ester | 7.0 |
| 2 | propranolol hydrochloride | N-methylpyrrolidone | " | 11.5 |
| 3 | propranolol hydrochloride | propylene glycol | proline n-octyl ester | 6.5 |
| 4 | propranolol hydrochloride | N,N-dimethylacetamide | " | 10.2 |
| 5 | propranolol hydrochloride | N-N'-dimethyl-ethyleneurea | proline n-decyl ester | 9.8 |
| 6 | propranolol hydrochloride | propylene glycol | " | 7.2 |
| 7 | propranolol hydrochloride | ethanol | proline n-docecyl ester | 7.6 |
| 8 | propranolol hydrochloride | N-methylpyrrolidone | " | 11.2 |
| 9 | propranolol hydrochloride | propylene glycol | " | 7.7 |
| 10 | propranolol hydrochloride | 1,2-propanediol | " | 6.8 |
| 11 | propranolol hydrochloride | methyl cellosolve | " | 5.3 |
| 12 | propranolol hydrochloride | N,N-dimethylacetamide | proline n-tetradecyl ester | 8.8 |
| 13 | propranolol | propylene glycol | proline n-tetradecyl | 5.4 |

TABLE 5-continued

| Example No. | (1) Active Ingredient | (2) Polar Compound | (3) Proline Ester (I) | Q value |
|---|---|---|---|---|
| 14 | propranolol hydrochloride | N,N'-dimethyl-ethyleneurea | proline n-octadecyl ester | 4.1 |
| 15 | propranolol hydrochloride | ethanol | proline n-octadecyl ester | 6.0 |
| 16 | propranolol hydrochloride | N-methylpyrrolidone | proline 2-ethylhexyl ester | 9.4 |
| 17 | propranolol hydrochloride | ethanol | proline 2-decenyl ester | 10.2 |
| 18 | propranolol hydrochloride | N-methylpyrrolidone | N-methylproline n-dodecyl ester | 10.0 |
| 19 | propranolol hydrochloride | ethanol | N-methylproline n-dodecyl ester | 7.7 |
| 20 | propranolol hydrochloride | propylene glycol | N-methylproline n-dodecyl ester | 8.6 |
| 21 | propranolol hydrochloride | N,N-dimethylformamide | N-methylproline n-dodecyl ester | 11.4 |
| 22 | propranolol hydrochloride | ethyl lactate | N-methylproline n-dodecyl ester | 4.9 |
| 23 | diazepam | N-methylpyrrolidone | proline n-dodecyl ester | 2.5 |
| 24 | " | propylene glycol | " | 2.1 |
| 25 | " | N-methylpyrrolidone | N-methylproline n-dodecyl ester | 3.0 |
| 26 | " | " | N-cyclohexylproline n-decyl ester | 1.8 |
| 27 | " | " | N-2-ethylhexylproline methyl ester | 1.5 |
| 28 | metoclopramide hydrochloride | propylene glycol | N-hexylproline methyl ester | 17.8 |
| 29 | metoclopramide hydrochloride | N-methylpyrrolidoine | N-dodecylproline ethyl ester | 21.4 |
| 30 | sodium salicylate | ethanol | N-dodecylproline ethyl ester | 2.2 |
| 31 | " | N,N-dimethylacetamide | N-hexadecylproline ethyl ester | 1.8 |
| 32 | indometachine | N,N'-dimethyl-ethyleneurea | proline n-dodecyl ester | 1.9 |
| 33 | " | ethanol | N-hexylproline hexyl ester | 2.1 |

TABLE 6

| Comparative Example No. | (1) Active Ingredient | (2) Polar Compound | Q Value |
|---|---|---|---|
| 1 | propranolol hydrochloride | propylene glycol | 0.73 |
| 2 | propranolol hydrochloride | N,N'-dimethyl-ethyleneurea | 0.51 |
| 3 | sodium salicylate | N,N-dimethylacetamide | 0.43 |
| 4 | indometacine | ethanol | 0.67 |
| 5 | metoclopramide hydrochloride | N-methylpyrrolidione | 0.68 |
| 6 | diazepam | " | 0.59 |
| 7 | " | N,N-dimethylformamide | 0.81 |

TABLE 7

| Example No. | Amount of N-methylpyrrolidone (wt %) | Amount of Proline n-Dodecyl Ester (wt %) | Q Value |
|---|---|---|---|
| 34 | 94 | 5 | 11.1 |
| 35 | 97 | 2 | 9.7 |
| 36 | 98 | 1 | 11.4 |
| 37 | 98.5 | 0.5 | 3.3 |

TABLE 8

| Example No. | Amount of N-Methyl pyrrolidone (wt %) | Amount of N-Methyl-proline n-Dodecyl Ester (wt %) | Q Value |
|---|---|---|---|
| 38 | 94 | 5 | 9.0 |
| 39 | 98 | 1 | 2.6 |
| 40 | 98.5 | 0.5 | 3.3 |

TABLE 9

| Example No. | (1) Active Ingredient | (2) Polar Compound | Q Value |
|---|---|---|---|
| 41 | propranolol hydrochloride | N-methyl-pyrrolidone | 5.7 |
| 42 | propranolol hydrochloride | ethanol | 6.4 |
| 43 | propranolol hydrochloride | propylene glycol | 4.3 |
| 44 | diazepam | N-methyl-pyrrolidone | 1.6 |
| 45 | " | ethanol | 1.3 |
| 46 | " | propylene glycol | 1.1 |

TABLE 10

| Example No. | (1) Active Ingredient | (2) Polar Compound | (3) Prolinol Ester (II) $R_3$ | $R_4$ | Q value |
|---|---|---|---|---|---|
| 47 | propranolol hydrochloride | N-methylpyrrolidone | H | n-$C_6H_{13}$ | 4.6 |
| 48 | " | ethanol | H | n-$C_8H_{17}$ | 5.7 |
| 49 | " | ethyl lactate | H | n-$C_{10}H_{21}$ | 4.9 |
| 50 | " | propylene glycol | H | n-$C_{12}H_{25}$ | 4.8 |

TABLE 10-continued

| Example No. | (1) Active Ingredient | (2) Polar Compound | (3) Prolinol Ester (II) R$_3$ | R$_4$ | Q value |
|---|---|---|---|---|---|
| 51 | " | N,N-dimethylformamide | H | n-C$_{14}$H$_{29}$ | 3.3 |
| 52 | " | N,N'-dimethylethyleneurea | H | 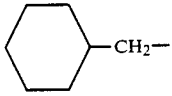 | 2.8 |
| 53 | " | 1,3-propanediol | H | 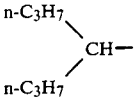 | 5.0 |
| 54 | " | N-methylpyrrolidone | H | $\begin{array}{c}C_2H_5\\|\\CH_3(CH_2)_3CH-\end{array}$ | 5.3 |
| 55 | " | " | CH$_3$ | CH$_3$(CH$_2$)$_7$CH=CH(CH$_2$)$_7$— | 4.1 |
| 56 | " | N,N-dimethylacetamide | CH$_3$ | CH$_3$(CH$_2$)$_4$CH=CHCH$_2$CH=CH(CH$_2$)$_7$ | 3.9 |
| 57 | " | ethanol | CH$_3$ | 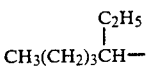 | 3.7 |
| 58 | " | " | CH$_3$ | $\begin{array}{c}C_2H_5\\|\\CH_3(CH_2)_3CH-\end{array}$ | 4.6 |
| 59 | " | N-methylpyrrolidone | C$_2$H$_5$ | CH$_3$(CH$_2$)$_4$CH=CH— | 5.0 |
| 60 | propranolol hydrochloride | propylene glycol | C$_2$H$_5$ | n-C$_7$H$_{15}$ | 3.2 |
| 61 | " | ethyl lactate | C$_2$H$_5$ | n-C$_{16}$H$_{33}$ | 2.4 |
| 62 | " | ethanol | n-C$_5$H$_{11}$ | n-C$_{10}$H$_{21}$ | 3.1 |
| 63 | " | 1,3-propanediol | n-C$_5$H$_{11}$ | n-C$_{11}$H$_{23}$ | 3.4 |
| 64 | " | N-methylpyrrolidone | n-C$_5$H$_{11}$ | n-C$_{13}$H$_{27}$ | 3.9 |
| 65 | diazepam | " | CH$_3$ | CH$_3$(CH$_2$)$_7$CH=CH(CH$_2$)$_7$— | 2.0 |
| 66 | " | N,N'-dimethylethyleneurea | CH$_3$ | n-C$_{12}$H$_{25}$ | 1.6 |
| 67 | " | propylene glycol | C$_5$H$_{11}$ | n-C$_{16}$H$_{21}$ | 1.3 |
| 68 | metoclopramide hydrochloride | ethanol | H | n-C$_6$H$_{13}$ | 8.7 |
| 69 | " | N-methylpyrrolidone | H | n-C$_8$H$_{17}$ | 9.8 |
| 70 | " | methyl lactate | CH$_3$ | $\begin{array}{c}C_2H_5\\|\\CH_3(CH_2)_3CH-\end{array}$ | 6.5 |
| 71 | indometachine | N,N-dimethylformamide | C$_2$H$_5$ | 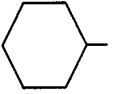 | 1.8 |
| 72 | " | N,N-dimethyl acetamide | CH$_3$ | n-C$_{12}$H$_{25}$ | 2.3 |
| 73 | indometachine | 1,3-propanediol | CH$_3$ | C$_5$H$_{11}$CH=CHCH$_2$CH=CH(CH$_2$)$_7$— | 1.4 |
| 74 | sodium salicylate | N-methylpyrrolidone | H | n-C$_{15}$H$_{31}$ | 2.2 |
| 75 | " | ethanol | CH$_3$ |  | 2.0 |
| 76 | " | propylene glycol | H | n-C$_{10}$H$_{21}$ | 1.7 |
| 77 | propranolol hydrochloride | N-methylpiperidone | H | n-C$_{12}$H$_{25}$ | 4.4 |
| 78 | " | butyrolactone | H | n-C$_{10}$H$_{21}$ | 3.8 |
| 79 | " | ethylene glycol monoethyl ether | CH$_3$ | n-C$_{12}$H$_{25}$ | 2.7 |
| 80 | " | α-monothioglycerol | CH$_3$ | n-C$_8$H$_{17}$ | 3.5 |
| 81 | " | glycerin monoacetate | CH$_3$ | n-C$_6$H$_{13}$ | 1.7 |

TABLE 11

| Comparative Example No. | (1) Active Ingredient | (2) Polar Compound | Q Value |
|---|---|---|---|
| 8 | propranolol hydrochloride | N,N'-dimethylethyleneurea | 0.29 |
| 9 | propranolol hydrochloride | N,N-dimethylacetamide | 0.36 |
| 10 | metoclopramide hydrochloride | propylene glycol | 0.02 |
| 11 | metoclopramide hydrochloride | ethanol | 0.80 |

TABLE 11-continued

| Comparative Example No. | (1) Active Ingredient | (2) Polar Compound | Q Value |
|---|---|---|---|
| 12 | sodium salicylate | N-methyl-pyrrolidone | 0.21 |
| 13 | " | N,N-dimethyl-acetamide | 0.43 |
| 14 | diazepam | propylene glycol | 0.36 |
| 15 | " | N,N-dimethyl-formamide | 0.81 |
| 16 | indometacine | ethanol | 0.32 |
| 17 | " | propylene glycol | 0.07 |

While the invention has been described in detail and with reference to specific embodiments thereof, it will be apparent to one skilled in the art that various changes and modifications can be made therein without departing from the spirit and scope thereof.

What is claimed is:

1. A method for enhancing percutaneous absorption of a pharmaceutically active compound comprising externally applying a medical composition to the skin of one in need thereof wherein said medical composition comprises:

(a) a proline ester represented by formula (I):

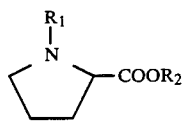

(I)

wherein $R_1$ represents a hydrogen atom or an aliphatic hydrocarbon residue, and $R_2$ represents an aliphatic hydrocarbon residue, with the total number of carbon atoms in $R_1$ and $R_2$ being 20 or less, or a prolinol ester represented by the formula (II):

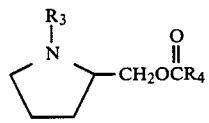

(II)

wherein $R_3$ represents a hydrogen atom or an aliphatic hydrocarbon residue, and $R_4$ represents an aliphatic hydrocarbon residue, with the total number of carbon atoms in $R_3$ and $R_4$ being 18 or less; and (b) a pharmaceutically active compound.

2. A method as claimed in claim 1, wherein said medical composition further comprises at least one polar compound and said polar compound is at least one compound having nonpharmaceutical activity selected from the group consisting of lower mono alcohols having from 1 to 6 carbon atoms, glycerin, glycerin esters selected from the group consisting of mono-esters, diesters and triesters, thioglycerols, lactic esters having from 1 to 4 carbon atoms in the alcohol moiety, ethyleneurea derivatives thereof represented by formula (V):

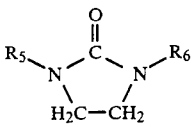

(V)

wherein $R_5$ and $R_6$ each represents a hydrogen atom or a lower alkyl group, amid compounds represented by formula (VI):

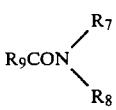

(VI)

wherein $R_7$, $R_8$, and $R_9$ each represents a hydrogen atom or a lower alkyl group, alkylene glycols, mono- or diethylene glycol monoalkyl esters, lactones, pyrrolidone compounds represented by formula (VII):

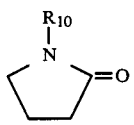

(VII)

wherein $R_{10}$ represents a hydrogen atom or a lower alkyl group, and lactam compounds represented by formula (VIII):

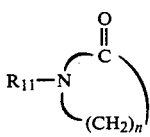

(VIII)

wherein $R_{11}$ represents a lower alkyl group; and n represents 4 or 5.

3. A method as claimed in claim 2, wherein said polar compound is present in an amount of from 30 to 99.5% by weight based on the total weight of the proline ester or prolinol ester and the polar compound.

4. A method as claimed in claim 2, wherein said pharmaceutically active compound is present in an amount of from 0.01% to 20% by weight based on the total weight of the proline ester or prolinol ester and the polar compound.

* * * * *